United States Patent
Jacobsen et al.

[11] Patent Number: 6,022,369
[45] Date of Patent: Feb. 8, 2000

[54] WIRE DEVICE WITH DETACHABLE END

[75] Inventors: Stephen C. Jacobsen, Salt Lake City; John Lippert, Park City; Clark Davis; Kent Backman, both of Salt Lake City, all of Utah

[73] Assignee: Precision Vascular Systems, Inc., Salt Lake City, Utah

[21] Appl. No.: 09/023,806

[22] Filed: Feb. 13, 1998

[51] Int. Cl.[7] .................................................. A61M 29/00
[52] U.S. Cl. ............................. 606/191; 606/1; 606/108
[58] Field of Search .......................... 606/1, 108, 151, 606/191, 194, 195; 604/22; 623/1

[56] References Cited

U.S. PATENT DOCUMENTS

| | | |
|---|---|---|
| 3,219,022 | 11/1965 | Hagemeyer . |
| 4,994,069 | 2/1991 | Ritchart et al. ...................... 606/191 |
| 5,108,407 | 4/1992 | Geremia et al. . |
| 5,122,136 | 6/1992 | Guglielmi et al. . |
| 5,250,071 | 10/1993 | Palermo ............................. 606/198 |
| 5,261,916 | 11/1993 | Engelson ........................... 606/108 |
| 5,304,195 | 4/1994 | Twyford, Jr. et al. ................ 606/191 |
| 5,350,397 | 9/1994 | Palermo et al. .................... 606/200 |
| 5,354,295 | 10/1994 | Guglielmi et al. . |
| 5,427,118 | 6/1995 | Nita et al. ........................... 600/585 |
| 5,540,680 | 7/1996 | Guglielmi et al. . |
| 5,569,245 | 10/1996 | Guglielmi et al. . |
| 5,746,769 | 5/1998 | Ton et al. ........................... 606/296 |
| 5,749,894 | 5/1998 | Engelson ........................... 606/213 |
| 5,800,453 | 9/1998 | Gia ..................................... 606/191 |
| 5,800,455 | 9/1998 | Palermo et al. .................... 606/191 |
| 5,814,062 | 9/1998 | Sepetka et al. .................... 606/198 |
| 5,851,206 | 12/1998 | Guglielmi et al. ................... 606/28 |
| 5,855,578 | 1/1999 | Guglielmi et al. ................... 606/32 |
| 5,891,128 | 4/1999 | Gia et al. ............................... 606/1 |
| 5,891,130 | 4/1999 | Palermo et al. ........................ 606/1 |
| 5,895,385 | 4/1999 | Guglielmi et al. ................... 606/32 |
| 5,895,391 | 4/1999 | Farnholtz ........................... 606/108 |

FOREIGN PATENT DOCUMENTS

| | | |
|---|---|---|
| 93/03677 | 11/1993 | WIPO . |
| 96/11031 | 1/1997 | WIPO . |
| 96/18995 | 6/1997 | WIPO . |

*Primary Examiner*—Linda C. M. Dvorak
*Assistant Examiner*—Brad C. Blaise
*Attorney, Agent, or Firm*—Thorpe, North & Western, LLP

[57] ABSTRACT

Apparatus and method are disclosed by which a distal end portion of a wire may be deposited at selected sites in body passageways. The apparatus includes an elongate wire having a distal end section for detachment and delivery to a target location, the wire also having a discontinuity located rearwardly of the distal end section for rupturing when vibrational energy is applied to the wire. Also included is a vibrational energy source couplable to the proximal end of the wire for selectively applying vibrational energy to the wire to travel to the discontinuity and cause detachment of the end section. The discontinuities may take the form of cuts formed in the wire, reduced diameter sections in the wire, adhesive, welded or soldered couplings between the wire and the distal end section, or the wire transitioning from the wire to a large mass disposed on the distal end section.

49 Claims, 3 Drawing Sheets

WIRE DEVICE WITH DETACHABLE END

BACKGROUND OF THE INVENTION

The present invention relates to a method and apparatus for threading wires into body cavities and detaching end sections of the wire using vibrational energy, for example, in the form of elastic waves.

A variety of methods have been developed for occluding and/or stabilizing and sealing off vasculature or body passageways, tissue defects and aneurysms with the use of endovascular catheters including injectable particles, injectable glue, and detachable coils and other devices. The use of detachable coils appears to be gaining widest acceptance for aneurysm therapy, perhaps because of the ease and precision of control of the delivery and disposition of the coil at the desired occlusion site.

One approach for delivering and detaching coils at an occlusion site involves forming or attaching the coil at the distal end of a wire, and then threading the coil and wire through a catheter until the coil is disposed at the occlusion site. An electric current is then applied to the proximal end of the wire and conducted through the wire to the point of origin or attachment of the coil where it causes the coil, for example, by electrolysis, to detach from the wire. See U.S. Pat. Nos. 5,569,245, 5,624,449, 5,122,136, 5,540,680, and 5,354,295.

Among the problems associated with the electrically detachable coil approach is the time necessary to effectuate detachment (which changes with increasing number of devices delivered), the lack of reliability that the coil will detach, discomfort with the use of a grounding needle (insertable in the flesh of the patient) required for the proper functioning of the device, generation of particulates from the detachment site (electrolysis), and inability to select the size of the coil in vivo.

SUMMARY OF THE INVENTION

It is an object of the invention to provide an apparatus and method of selectively detaching an end section of a wire in a body passageway by non-electrical means.

It is also an object of the invention to provide such an apparatus and method in which the end section of the wire may be quickly and reliably detached, independently of the number of devices delivered.

It is a further object of the invention to provide such an apparatus and method in which little discomfort results to the patient.

It is still another object of the invention to provide such an apparatus and method, in accordance with one aspect thereof, in which multiple sections of the end segment of the wire may each be selectively detached at different times.

It is an additional object of the invention to provide such an apparatus and method, in accordance with another aspect thereof, in which it may readily be determined by the user when the end section of the wire has detached.

It is a further object of the invention to provide such an apparatus and method in which little preparation of the wire and end section is required to allow for subsequent use and detachment of the end segment.

It is also an object of the invention to provide such an apparatus and method having various types of lightweight end sections.

The above and other objects of the invention are realized in a specific illustrative embodiment of a wire apparatus with detachable distal end which includes an elongate wire (either solid or hollow) having a distal end section, and a discontinuity located rearwardly of the distal end section for rupturing when vibrational energy is applied thereto, and a vibrational energy generator for applying vibrational energy to the wire to travel to discontinuity and cause detachment of the distal end section. In use, the wire would be threaded through a vasculature or body passageway to a target location, and then vibrational energy would be applied to the wire to cause the distal end section to detach at the target location, for example, to occlude the passageway.

In accordance with one aspect of the invention, the discontinuity could include a cut in the wire, a hole, a reduced diameter section, an abrupt increase in mass, an adhesive, soldered or spot-welded joint which joins the distal end section to the wire, or a heat or chemically treated section.

In accordance with another aspect of the invention, the distal end section could include a plurality of discontinuities, each adapted to rupture at a different vibrational level or frequency, to detach that portion of the distal end section which is distal to the discontinuity being ruptured.

In accordance with still another aspect of the invention, the vibrational energy generator constitutes an ultrasound generator.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
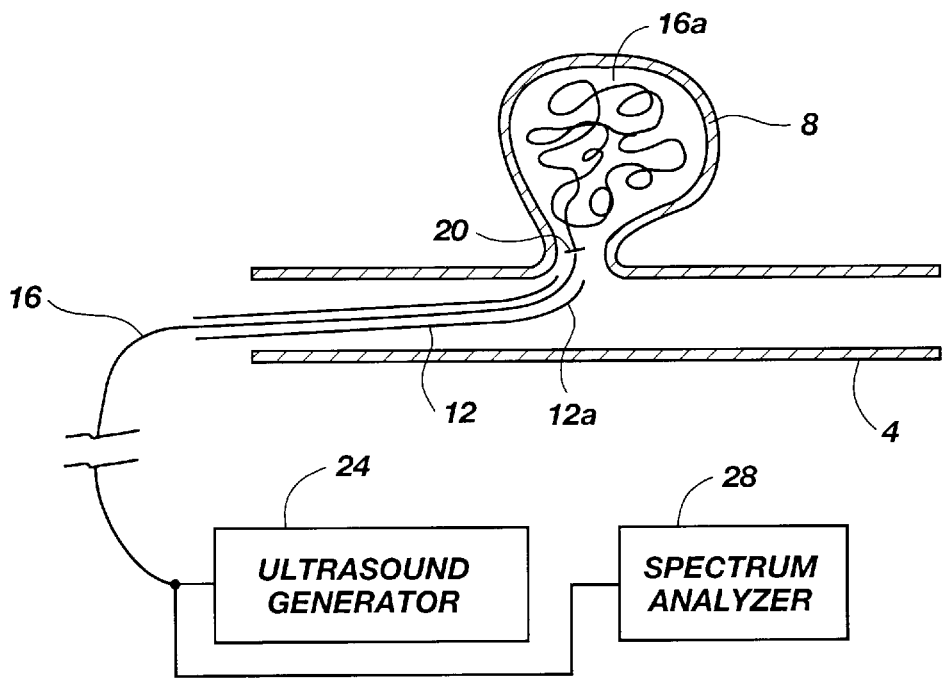
FIG. 1 shows a side, fragmented, cross-sectional view showing a wire made in accordance with the principles of the present invention, disposed in a catheter in a blood vessel in which the proximal end of the wire is coupled to an ultrasound generator and the distal end of the wire is formed into a tangled mass disposed in an aneurysm.

Reference will now be made to the drawings in which the various elements of the present invention will be given numeral designations and in which the invention will be discussed so as to enable one skilled in the art to make and use the invention. Referring to FIG. 1, there is shown a side, cross-sectional view of a blood vessel 4 in which an aneurysm 8 is shown formed in one side of the vessel.

A fragmented view of a catheter 12 is shown threaded in the vessel 4, with a terminal end 12a positioned adjacent the aneurysm 8. Threaded through the catheter 12 is a wire 16 ("wire" may be taken to mean any long prismatic element, solid or hollow), which extends entirely through the catheter 12 and out the terminal end 12a into the aneurysm 8 (or the entrance thereof) to substantially fill the aneurysm with a coiled end section 16a (the end section 16a could be tangled, formed into specific shapes, etc. as well as being coiled) of the wire 16. What will be called a discontinuity 20 is formed between the end section 16a of the wire and the rest of the wire 16. The discontinuity 20 may take a variety of shapes and structures, but all are designed to rupture, break or separate when vibrational energy is applied to the wire 16. The vibrational energy source in the FIG. 1 embodiment is an ultrasound generator 24, but could be something as simple as a striker, mallet, hammer, etc. for striking the wire 16 to cause a vibration or mechanical energy to propagate to the discontinuity 20.

In use, the catheter 20 is threaded through a vasculature or body passageway to a site at which the end section 16a of the wire is to be disposed, such as the aneurysm 8 in FIG. 1. The purpose of such disposal, for example, is to provide an occlusion in the passageway to allow for coagulation of blood to prevent further flow, or, as in the FIG. 1 schematic, to cause scarring in the aneurysm 8 to thereby fill the aneurysm with scar tissue to prevent the bursting thereof, etc. The end section 16a is shown as being coiled or tangled but when threaded through the catheter 12 it would be straightened but then when pushed out the terminal end 12a of the catheter, the end section would resume the normally coiled or tangled condition as shown (enhanced also by body warmth).

After the end section 16a has been guided to the desired target site, the ultrasound generator 24 would be connected to the proximal end of the wire 16 and an ultrasound signal applied thereto. The frequency and amplitude of the signal (observed on a spectrum analyzer 28) would be selected to produce high stress in the discontinuity 20, fatiguing the wire so that it breaks, ruptures, or otherwise separates at the discontinuity, leaving the end section 16a in the aneurysm 8. The separation is accomplished rapidly, reliably and without pain to the subject.

Figure 2:
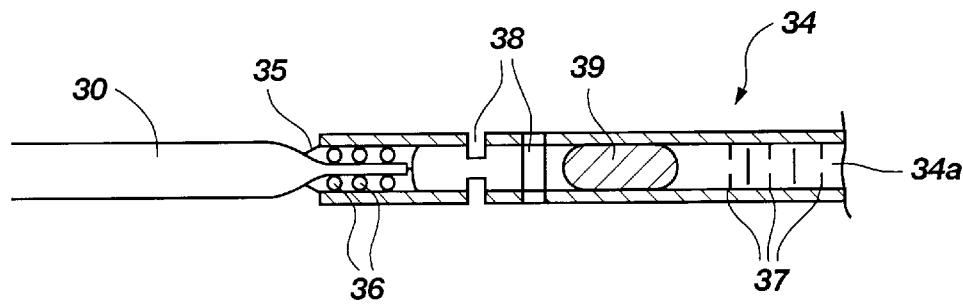
FIGS. 2–3, 4a–4c, and 5–6 show side, fragmented views of different embodiments for providing discontinuities to allow detachment of end coil sections from delivery wires, all in accordance with the principles of the present invention.

FIG. 2 shows a fragmented, side, cross-sectional view of a wire 30 made, for example, of stainless steel, connected to a tubular end section 34 made, for example, of nickel titanium alloy or platinum. The terminal end of the wire 30 is tapered, as shown, and is inserted into a hollow 34a in the proximal end of the end section 34, and there secured by an adhesive, solder or weld 35. A coil 36 made, for example, of stainless steel is soldered, welded or otherwise attached to the terminal end of the wire 30 to enhance the bond between the wire and the end section 34.

The end section 34 includes a plurality of cuts 37 made to extend generally transversely in the end section and provided to shape the end section into a coiled or tangled configuration, and to allow for more surface area exposure of the end section to blood for inducing clotting. See co-pending U.S. patent application Ser. No. 08/568,493, filed Dec. 7, 1995, for a further discussion of the employment of cuts in wire to allow flexibility and control shape while maintaining torquability. Two or more cuts 38 (rotated 90 degrees with respect to one another) are shown spaced rearwardly from the plurality of cuts 37 by a distance greater than the spacing between the cuts 37, and are provided to serve as the discontinuity for rupturing (fatigue) when a vibrational signal is applied to the wire 30. The cuts 38, of course, could be formed at the same time the other cuts 37 are being formed but, for example, would be made deeper (thinner beam), wider, or adjacent a mass 39 disposed in the end section 34, or a combination, to sever or rupture when the vibrational signal is applied to the wire 30.

Figure 3:
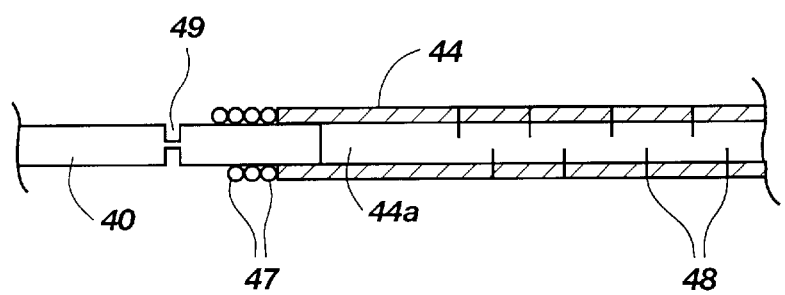

FIG. 3 shows a fragmented, side, cross-sectional view of another embodiment a wire with discontinuity in accordance with the present invention. Here, a wire 40 made, for example, of stainless steel, is fitted into the hollow 44a of an end section 44 made, for example, of nickel-titanium alloy. The wire 40 would be held in place in the hollow by a suitable adhesive, such as epoxy or cyanoacrylate. A plurality of cuts 48 are made in the end section 44 to provide for coiling and configuring the end section as desired for ultimate disposition at a target site in a body passageway. A cut or diameter reduction 49 is also formed in the wire 40 to provide the desired discontinuity. A coil mass 47 might also be added about the wire 40 to further exaggerate the discontinuity. The cut 49 might advantageously be about ½ of the way through the wire 40 in the transverse direction to serve to rupture or separate when an ultrasound signal is applied to the wire.

Figure 4A:
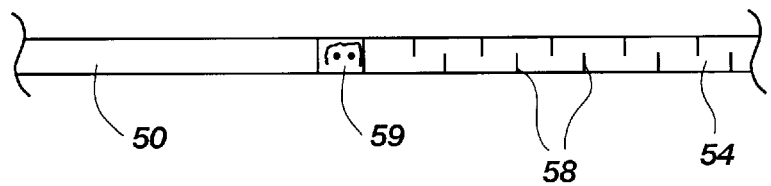

FIG. 4A shows another embodiment of a discontinuity between a wire 50 and an end section 54, again including cuts 58. The terminal end of the wire 50 is attached by a section of adhesive 59 to the proximal end of the end section 54. The adhesive 59 is selected to be somewhat brittle, for example, sodium silicate, so that when an ultrasound signal is applied to the wire 50, the adhesive 59 will fracture to allow the end section 54 to separate from the wire 50.

Alternatively, the section 59 of the wire 50 could be a heat-treated (including H+embrittlement) section to make the wire brittle at that location, or a chemically-treated section, for example etched, to make the wire weaker at the location.

Figure 4B:
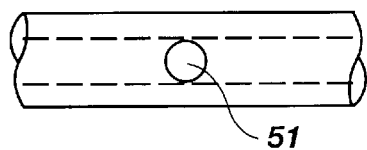
Figure 4C:
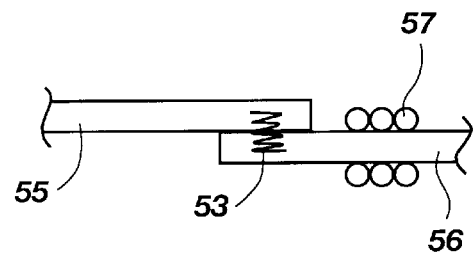

FIG. 4B shows the discontinuity formed as a hole 51, whereas FIG. 4C shows the discontinuity as a spot weld 53 joining the wire 55 side-by-side to an end section 56. A coil mass 57 provides additional discontinuity. The process of spot welding heats the wire 55 making it more susceptible to fatigue and breaking. In fact, heating alone may be used to create a "discontinuity".

Figure 5:
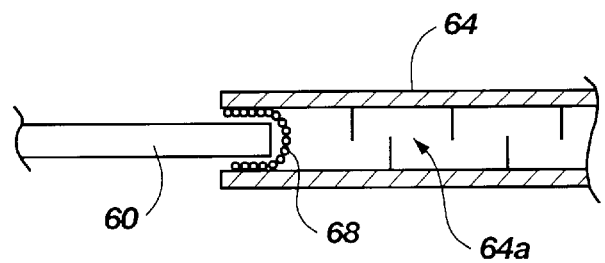

FIG. 5 shows an embodiment similar to that of FIG. 3 except that the discontinuity does not comprise a cut in either the wire 60 or end section 64. Rather, the discontinuity is formed at the joint or connection between the wire 60 and end section 64 wherein the wire is inserted in the hollow 64a of the end section and held in place by a blood soluble adhesive 68, such as sodium silicate. When the end section 64 is guided through a blood vessel by the wire 60 (i.e., through a catheter inserted in a blood vessel), blood enters the hollow 64a of the end section 64 which, along with blood contacting the adhesive 68 at the proximal end of the end section, operates to dissolve the adhesive and allow separation of the end section from the wire.

Application of a vibrational signal such as an ultrasound signal to the wire 60 accelerates the dissolution and ultimate separation of the end section 64 from the wire 60 to allow disposition of the end section at the target site. In effect, two mechanisms may be employed to cause separation— providing greater security and safety in ensuring separation.

Figure 6:
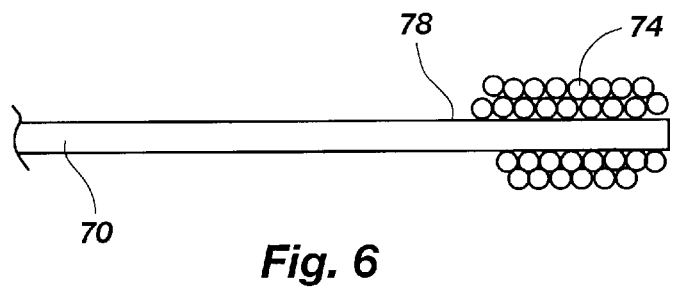

The FIG. 6 embodiment includes a wire 70 at the distal end of which is disposed a heavy mass of material 74, preferably wound about the distal end. For example the mass 74 might include windings of platinum.

The abrupt transition from the wire 70 to the heavy mass 74 provides a discontinuity at location 78 just behind the mass so that when vibrational energy of a certain frequency and amplitude is applied to the wire, the wire is caused to break at the discontinuity or stress point 78, releasing the mass 74 at a target site in a body passageway. The wire 70 might also be made of platinum, stainless steel or nickel titanium alloy.

Figure 7:
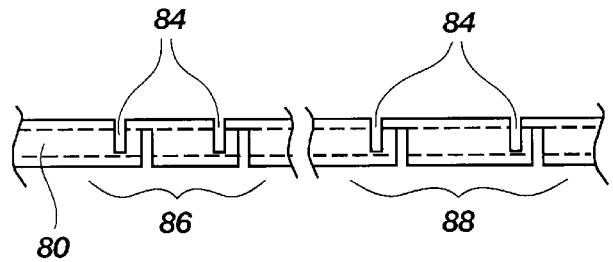
FIG. 7 is a side, fragmented view of end coil sections having a plurality of discontinuities for tuned resonator detachment, in accordance with the principles of the present invention.

FIG. 7 shows an embodiment of a detachable wire 80 having a plurality of longitudinally spaced-apart cuts 84 in sections 86 and 88, which act as separate discontinuities. The discontinuities 84 of section 86 are formed or "tuned" with a predetermined depth, width, and/or spacing to rupture in response to different amplitudes and frequencies of vibrational energy than the discontinuities of Section 88. In this manner, the user can selectively apply vibrational energy to the wire 80 to cause a selected section of the discontinuities 84 to rupture. Such rupturing can take place successively to deposit lengths of wire at different locations in a body passageway or to deposit all of the lengths (to serve as emboli) at a single location. The "tuning" of the discontinuities 84 is a function of the characteristics of the cuts, but also the segment lengths between the discontinuities. Such timing could be used to "deposit" great numbers of particles such as for AVM therapy.

The cuts 84 create spring elements to isolate the intermediate uncut sections of the wire 80 which have a mass. When a vibrational energy wave at the resonant frequency of the spring/mass system is applied to the wire 80, the wire is excited longitudinally and the sections of mass between the cuts vibrate longitudinally at high amplitude which fatigues the spring elements (location of cuts) causing them to break. The wire 80 could advantageously be made of stainless steel or nickel titanium alloy.

Figure 8:
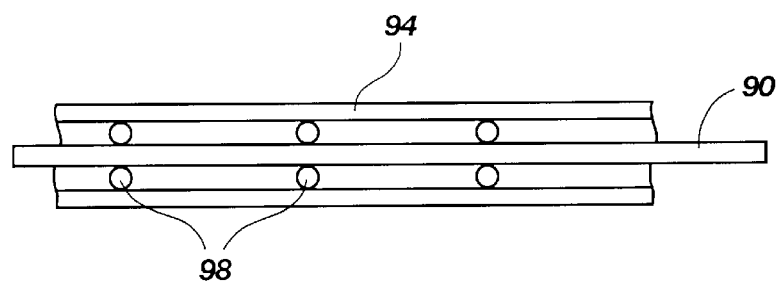
FIGS. 8 and 9 show side, fragmented views of embodiments guide wire/catheter combinations where friction between the guide wire and catheter is minimized.
Figure 9:
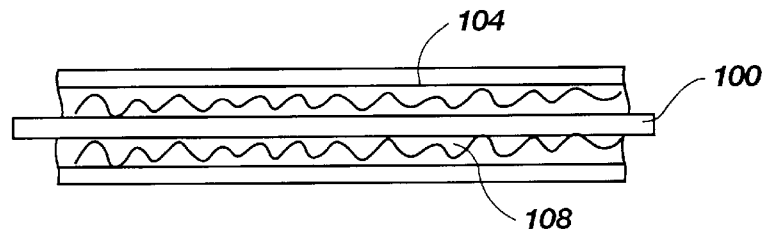

FIGS. 8 and 9 show side, cross-sectional, fragmented views of a type of wave guide construction for transmitting vibrational energy along a wire surrounded by a catheter or sleeve. Referring to FIG. 8, there is shown a wire 90 disposed inside of a catheter or sleeve 94 but held out of touch from the sleeve by supports, for example, in the form of balls, spaced apart longitudinally and uniformly along the length of the wire and sleeve. The supports 98 are positioned at the velocity nodal points of the vibrational energy waves which are transmitted along the wire/sleeve combination to cause detachment of an end section (not shown). The velocity nodal points, of course, are those locations in a mechanical wave where there is little or no movement or velocity of the wave-carrying structure, whereas the locations midway between the supports 98 are the so-called antinodes where there is maximum movement of the wave-carrying structure. By providing the supports 98, the wire and sleeve are held apart to thereby prevent friction between the two as the vibrational energy wave travels down the wire/sleeve combination. Thus, little energy is lost along the length of the wire and sleeve and so detachment of the end section would take less time.

FIG. 9 is a side, cross-sectional, fragmented view of a wire 100 about which is disposed a sleeve 104 and between which is disposed a hydrophillic coating or lubricant 108 to allow the wire and sleeve to move relative to one another without significant friction and thus without loss of vibrational energy.

Figure 10:
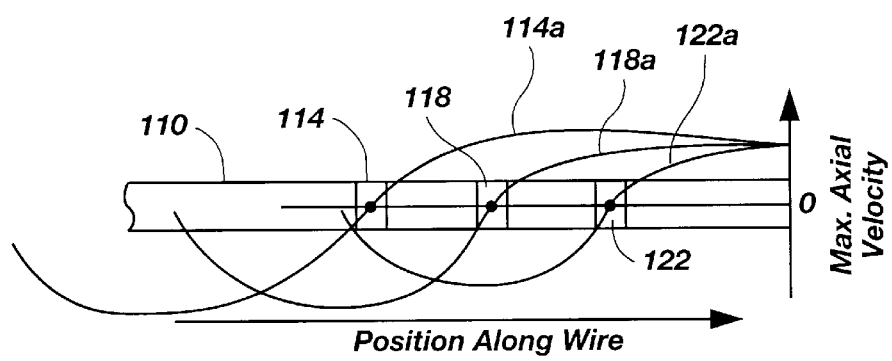
FIG. 10 is a graphic view of a wire illustrating nodal points responsive to different vibrational frequencies for detachment of end sections.

FIG. 10 shows a graphic representation of a wire 110 having discontinuities 114, 118 and 122 spaced longitudinally along the wire. Graphically superimposed over the wire 110 are three vibrational energy waves 114a, 118a, and 122a. In order to cause the wire 110 to separate at one of the selected discontinuities, a vibrational energy wave is applied to the wire so that the nodal point of the wave falls at the desired discontinuity. A vibrational energy wave causes mechanical resonance in the longitudinal direction where nodal points fall at locations which are spaced every one half of the wavelength. As briefly mentioned earlier, at the nodal points along the wire, the velocity or movement of the wire is minimal but the stress is maximal and so by applying a vibrational energy wave such as wave 114a to the wire 110, since a nodal point of wave 114a occurs at discontinuity 114, the wire would be caused to separate at that location where the greatest stress is occurring and the wire is weakest. Similarly, if it were desired that the separation occur at discontinuity 118, then vibrational energy wave 118a would be applied to the wire, etc. In the manner described, appropriate mechanical energy waves can be applied to wires to cause separation at selected discontinuities along the wire.

The various embodiments described above can be used to occlude blood flow, create scar tissue in aneurysms, in a known manner, but the embodiments could also be used to detach any type of end section device, such as a tubal block, in a body passageway, for example a fallopian tube, to block passage of eggs, or detach elements containing drugs for delivery to a target site, etc. That is, the embodiments are not limited solely to use in vasculature passageways.

It would be desirable to know immediately when the end section of a wire has been detached from the wire so that the wire can be withdrawn from the body passageway. For each of the embodiments described above involving a delivery wire portion and an end section for ultimate detachment at a target site, the combinations of wire and end sections all have natural or resonant frequencies. Thus, when vibrational energy is applied to a wire, such as wire 16 in FIG. 1, the resonant frequency of the combination of the wire 16 and end section 16a will have a certain resonant frequency which can be detected by conventional spectrum analysis methods. This resonant frequency is displayed on the spectrum analyzer 28 but as soon as the end section 16a of the wire 16 is detached from the wire, the resonant frequency of just the wire portion is different and, of course, will be displayed on the analyzer 28. Thus, a simple observation of the resonant frequency display on the analyzer 28 will provide a user with instantaneous information as to when the end section or coil has been detached. In place of spectrum analyzer 28, a microcontroller could be provided to monitor the resonant frequencies and signal a change in the frequency by lighting a lamp or sounding an alarm.

In the manner described, a method and apparatus have been described by which an end section of a wire may be easily, reliably and quickly detached from the delivery portion of the wire, generally without pain to the subject. The detached end section may be in the form of a coil, mass or other device and may be deposited in vasculature passageways or other body passageways. Vibrational energy is used to rupture discontinuities separating the delivery portion of the wire from the end section and so no electrical current of any kind is required, making it much safer for the subject.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. Wire apparatus with detachable distal end comprising an elongate wire, including a distal end section for delivery to and detachment at a target body location, said wire including a discontinuity located rearwardly of the distal end section for rupturing when vibrational energy is applied thereto, and
means for selectively applying vibrational energy to the wire to travel to the discontinuity and cause detachment of the distal end section.

2. Apparatus as in claim 1 wherein the discontinuity comprises a cut in the wire.

3. Apparatus as in claim 1 wherein the discontinuity comprises a reduced diameter section.

4. Apparatus as in claim 1 wherein the discontinuity comprises a heat-treated section to weaken the wire.

5. Apparatus as in claim 1 wherein the discontinuity comprises a chemically-treated or H+ embrittled section to weaken the wire.

6. Apparatus as in claim 5 wherein the section is chemically etched.

7. Apparatus as in claim 1 wherein the discontinuity comprises a hole extending through the wire.

8. Apparatus as in claim 1 wherein the discontinuity comprises an abrupt mass of material in or on the wire.

9. Apparatus as in claim 1 wherein the wire includes a first section extending from the proximal end to a terminal end, and wherein the distal end section is coupled to the terminal end, such coupling forming the discontinuity.

10. Apparatus as in claim 9 further including an adhesive joining the distal end section to the terminal end of the first section.

11. Apparatus as in claim 10 wherein said adhesive is blood soluble.

12. Apparatus as in claim 11 wherein said adhesive comprises a sugar-based adhesive.

13. Apparatus as in claim 10 wherein said adhesive forms a brittle joint.

14. Apparatus as in claim 13 wherein said adhesive comprises water-soluble glass adhesive.

15. Apparatus as in claim 9 further including solder joining the distal end section to the terminal end of the first section.

16. Apparatus as in claim 9 further including a welded joint joining the distal end section to the terminal end of the first section.

17. Apparatus as in claim 1 wherein the wire includes a first section extending from the proximal end to a terminal end, wherein the distal end section is coupled to the terminal end, and wherein the distal end section includes a plurality of generally transverse cuts spaced apart longitudinally along the distal end section for controlling the lateral flexibility of the distal end section, with at least one of the cuts being closer to the coupling between the first section and distal end section than the other cuts and being spaced a predetermined distance from the other cuts, said at least one cut forming the discontinuity.

18. Apparatus as in claim 17 wherein said at least one cut is deeper than the other cuts.

19. Apparatus as in claim 17 wherein said at least one cut is wider than the other cuts.

20. Apparatus as in claim 17 wherein said first section is constructed of stainless steel, and wherein said distal end section is constructed of nickel-titanium alloy.

21. Apparatus as in claim 17 wherein said at least one cut is cut to a depth to readily cause rupturing of the distal end section at the location of the at least one cut when the vibrational energy is applied thereto.

22. Apparatus as in claim 1 wherein the wire, except for the distal end section, is formed of stainless steel, and wherein the distal end section is formed of nickel-titanium alloy.

23. Apparatus as in claim 1 wherein the vibrational energy applying means comprises an ultrasound generator coupleable to the proximal end of the wire.

24. Apparatus as in claim 1 wherein the vibrational energy applying means comprises means by which the proximal end of the wire may be mechanically struck.

25. Apparatus as in claim 1 wherein the wire is a solid wire.

26. Apparatus as in claim 1 wherein the wire is a tubular wire.

27. Vascular occlusion apparatus comprising:
a wire for threading into a vasculature passageway to an occlusion site,
a distal end coupled to the wire and adapted for detachment when mechanical energy is applied to the proximal end of the wire;
discontinuity means located at or near the coupling of the distal end of the wire, configured to break when mechanical energy is applied thereto; and
a mechanical energy generator attachable to the proximal end of the wire for selectively applying mechanical energy thereto, to cause detachment of the distal end for disposition at the occlusion site.

28. Apparatus as in claim 27 wherein said discontinuity means is located in the wire.

29. Apparatus as in claim 27 wherein said discontinuity means is located in the distal end.

30. Apparatus as in claim 27 wherein the discontinuity means comprises a generally transverse cut.

31. Apparatus as in claim 27 wherein the discontinuity means comprises a brittle adhesive joint coupling the distal end to the wire.

32. Apparatus as in claim 27 wherein the discontinuity means comprises a blood soluble adhesive joint coupling the distal end to the wire.

33. Apparatus as in claim 27 wherein the discontinuity means comprises a solder joint coupling the distal end to the wire.

34. Apparatus as in claim 27 wherein the discontinuity means comprises a welded joint coupling the distal end to the wire.

35. Apparatus as in claim 27 wherein the discontinuity means comprises a reduced diameter section of the wire.

36. Apparatus as in claim 27 wherein the discontinuity means comprises a heat treated weakened section of the wire.

37. Apparatus as in claim 27 wherein the discontinuity means comprises a chemically etched section of the wire.

38. Apparatus as in claim 27 wherein the discontinuity means comprises a mass attached to the wire.

39. Apparatus as in claim 27 wherein the distal end is comprised of a material formed to coil when unconstrained, and selected from the group consisting of nickel-titanium alloy and platinum.

40. Apparatus as in claim 27 wherein the mechanical energy generator comprises an ultrasound generator, wherein the wire and distal end, when coupled, exhibit a first resonant frequency when ultrasound energy is applied thereto, and a second resonant frequency when the distal end is detached, said apparatus further including means attachable to the proximal end of the wire for detecting and displaying the resonant frequency exhibited by the wire.

41. Apparatus as in claim 27 wherein the discontinuity comprises a mass disposed at the distal end having a mass sufficiently greater than the mass of the wire such that the distal end mass detaches from the wire when mechanical energy is applied to the proximal end of the wire.

42. Apparatus as in claim 41 wherein the distal end mass is comprised of platinum.

43. Apparatus for selectively occluding body cavities comprising
a wire for threading to a body cavity, said wire including a distal end section having a plurality of spaced-apart discontinuities to define segments therebetween, each discontinuity adapted to sever when a selected vibrational energy frequency is applied thereto, and means for applying selected vibrational energy frequencies to a proximal end of the wire to cause at least some of the discontinuities to sever and thus detach the segment or segments located distally of the severed discontinuities.

44. Apparatus as in claim 43 wherein each discontinuity is adapted to sever in response to a different energy frequency.

45. Apparatus as in claim 43 wherein the vibrational energy frequency applying means comprises an ultrasound generator.

46. Apparatus as in claim 43 wherein the vibrational energy frequency applying means is adapted to apply vibrational energy frequencies to the wire such that one or more selected discontinuities are caused to rupture.

47. A method of disposition of an occlusive element at a target location in a vasculature passageway comprising (a) threading an elongate wire into the vasculature passageway so that a distal end, forming an occlusive element, is disposed at the target location, said distal end being detachable from the wire when an ultrasound signal is applied to the wire, (b) applying an ultrasound signal to the wire to cause the distal end thereof to detach at the target location, and (c) withdrawing the wire from the vasculature passageway, leaving the distal end at the target location.

48. A method of detaching the terminal end of a wire in a vasculature target site comprising the steps of (a) guiding the terminal end of the wire to the target site, and (b) applying an ultrasound signal to the wire so as to cause the terminal end thereof to detach at the target site.

49. A method as in claim 48 wherein step (b) comprises applying the ultrasound signal to a discontinuity formed in the wire proximally of the terminal end.

* * * * *